United States Patent
Lim et al.

(10) Patent No.: US 9,119,787 B2
(45) Date of Patent: *Sep. 1, 2015

(54) MICROPARTICLES FOR THE TREATMENT OF DISEASE

(75) Inventors: Florencia Lim, Union City, CA (US); Mikael Trollsas, San Jose, CA (US); Michael Ngo, San Jose, CA (US); Thierry Glauser, Redwood City, CA (US); Jinping Wan, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 768 days.

This patent is subject to a terminal disclaimer.

(21) Appl. No.: 12/806,790

(22) Filed: Aug. 19, 2010

(65) Prior Publication Data

US 2010/0323019 A1    Dec. 23, 2010

Related U.S. Application Data

(63) Continuation of application No. 12/132,562, filed on Jun. 3, 2008, now abandoned.

(51) Int. Cl.
*A61K 9/16* (2006.01)
*A61K 9/50* (2006.01)
*A61K 9/00* (2006.01)

(52) U.S. Cl.
CPC ............. *A61K 9/1647* (2013.01); *A61K 9/0019* (2013.01); *A61K 9/5031* (2013.01)

(58) Field of Classification Search
CPC .................................. A61K 9/16; A61K 9/50
See application file for complete search history.

(56) References Cited

U.S. PATENT DOCUMENTS

| | | | |
|---|---|---|---|
| 5,622,657 A * | 4/1997 | Takada et al. | 264/4.32 |
| 8,512,737 B1 * | 8/2013 | Consigny et al. | 424/426 |
| 2002/0054912 A1 | 5/2002 | Kim et al. | |
| 2005/0152942 A1 | 7/2005 | Hezi-Yamit et al. | |
| 2006/0018872 A1 | 1/2006 | Tew et al. | |
| 2006/0034925 A1 * | 2/2006 | Au et al. | 424/468 |
| 2006/0094674 A1 * | 5/2006 | Neel et al. | 514/44 |
| 2006/0189941 A1 * | 8/2006 | Seward et al. | 604/164.03 |
| 2008/0051335 A1 | 2/2008 | Kleiner et al. | |

FOREIGN PATENT DOCUMENTS

| | | |
|---|---|---|
| EP | 1 795 185 | 6/2007 |
| WO | WO 2004/110347 | 12/2004 |
| WO | WO 2005/035088 | 4/2005 |
| WO | WO 2005/117836 | 12/2005 |
| WO | WO 2007/055561 | 5/2007 |

OTHER PUBLICATIONS

T Kato, R Nemoto, H Mori, I Kumagai. "Microencapsulated Mitomycin-C Therapy in Renal-Cell Carcinoma." The Lancet, 314(8140) Sep. 1, 1979, pp. 479-480.*

(Continued)

*Primary Examiner* — Isaac Shomer
(74) *Attorney, Agent, or Firm* — Squire Patton Boggs (US) LLP

(57) ABSTRACT

Microparticle-bioactive agent based treatments for local treatment of diseased tissues/organs are disclosed.

20 Claims, 1 Drawing Sheet

(56) References Cited

OTHER PUBLICATIONS

N Lloberas, JM Cruzado, M Franquesa, IH Fresneda, J Torras, G Alperovich, I Rama, A Vidal, JM Grinyo. "Mammalian Target of Rapamycin Pathway Blockade Slows Progression of Diabetic Kidney Disease in Rats." Journal of the American Society of Nephrology, vol. 17, 2006, pp. 1395-1404.*

CS McArdle, H Lewi, D Hansell, DJ Kerr, J McKillop, N Willmott. "Cytotoxic-loaded Albumin Microspheres: A Novel Approach to Regional Chemotherapy." British Journal of Surgery, vol. 75, Feb. 1988, pp. 132-134.*

F Nijsen. "Radioactive holmium poly(L-lactic acid) microspheres for treatment of liver malignancies." PhD Thesis, Utrecht University, Apr. 2001. Four cover pages and pp. 31-44 are included.*

NS Nahman Jr., WT Drost, UY Bhatt, TJ Sferra, A Johnson, P Gamboa, GH Hinkle, A Haynam, V Bergdall, C Hickey, JD Bonagura, L Brannon-Peppas, JS Ellison, A Mansfield, S Shie, N Shen. "Biodegradable Microparticles for in vivo Glomerular Targeting: Implications for Gene Therapy of Glomerular Disease." Biomedical Microdevices, 4:3, 2002, pp. 189-195.*

LC Chen, ZR Wang, CM Wan, J Xiao, HL Guo, C Cornelissen, F Halberg. "Circadian renal rhythms influenced by implanted encapsulated hANP-producing cells in Goldblatt hypertensive rats." Gene Therapy, vol. 11, 2004, pp. 1515-1522.*

De et al., "Polycarboxylic acid nanoparticles for ophthalmic drug delivery: an ex vivo evaluation with human cornea", J. of Microencapsulation vol. 21, No. 8, pp. 841-855 (2004) Abstract only.

Farhood et al., "Cationic Liposomes for Direct Gene Transfer in Therapy of Cancer and othe Diseases", Gene Therapy for Neoplastic Diseases vol. 716, 3 pgs. (1994).

Ponchel et al. "Study of the interactions between nanoparticles and intestinal mucosa" Abstract, Book, vol. 97, 1 pg. (1994).

Shahiwala et al., "Nanocarriers for Systemic and Mucosal Vaccine Delivery", Recent Patents on Drug Delivery & Formulation pp. 1-9 (2007).

KM Shakesheff et al., "The Absorption of Poly(Vinyl Alcohol) to Biodegradable Microparticles Stidued by X-Ray Photoelectron Spectroscopy (XPS)" J. of Colloid and Interface Science 185, pp. 538-547 (1997).

Mallarde et al., "PLGA-PEG microspheres of teverelix: influence of polymer type on microsphere characteristics and on teverelix in vitro release", Int. J. of Pharmaceutics 261 pp. 69-80 (2003).

Lactide Materials Safety Data Sheet, (Apr. 24, 2003, Polysciences Inc).

Ethylene Glycol Mat. Safey Data Sheet (JTBaker, Mar. 15, 2004, www.electracool.com/MSDS-ETHYLENE-GLYCOL.pdf).

Glycolic Acid Mat. Safety Data Sheet (ScienceLab.com, Oct. 10, 2005, www.sciencelab.com/xMSDS-Glycolic_acid-9927181).

International Search Report for PCT/US2009/046006, mailed Oct. 22, 2010, 14 pgs.

Ito et al., "Incorporation of water-soluble drugs in PLGA microspheres" Colloids and Surfaces, J. Colsurf vol. 54, No. 2, pp. 173-178 (2007).

Pines et al., "Halofuginone: A novel antifibrotic therapy", Gen. Pharm. vol. 30, No. 4, pp. 445-450 (1998).

Shiga et al., "Preparation of Poly(D,L-Lactide) and Copoly(Lactide-Glycolide) Microspheres of Uniform Size", J. of Pharmacy and Pharmacology, vol. 48, No. 9, pp. 891-895 (1996).

Zweers et al., "Release of anti-restenosis drugs from poly(ethylene oxide)-poly(dl-lactic-co-glycolic acid) nanoparticles", J. of controlled release, vol. 114, No. 3, pp. 317-324 (2006).

* cited by examiner

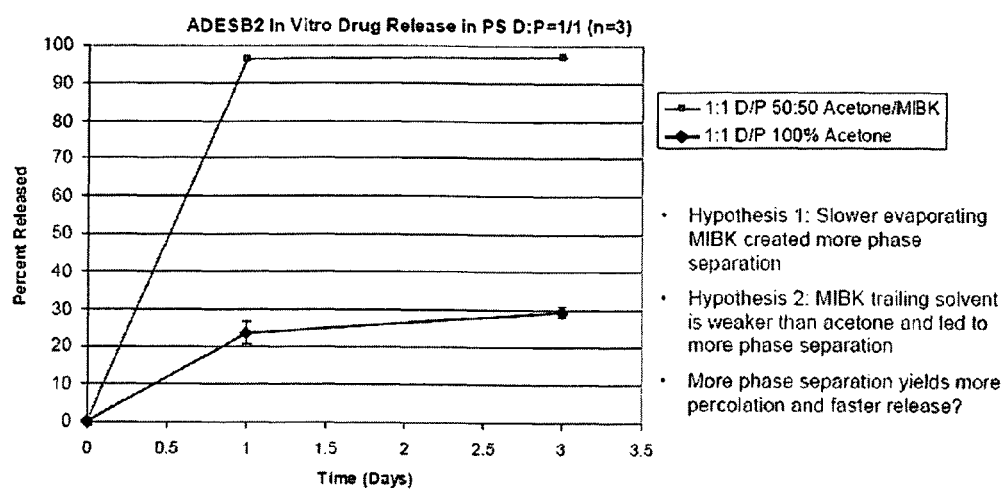

MICROPARTICLES FOR THE TREATMENT OF DISEASE

CROSS REFERENCE TO RELATED APPLICATIONS

This is a continuation application of U.S. patent application Ser. No. 12/132,562, filed Jun. 3, 2008, which application is incorporated, including any drawings, as if fully set forth herein.

FIELD

The present invention relates to drug delivery systems that include bioactive-agent loaded microparticles and methods of using them for the treatment of tissue or organ specific diseases.

BACKGROUND

Delivery of drug to a specific treatment site represents a substantial challenge in the design of drug delivery systems. While drugs designed for action at or within a specific tissue or organ, e.g., the kidney, may be suitable for systemic delivery, the amount of drug delivered by this route often must be quite high if a therapeutically effective amount is to be delivered to the desired site. Delivery of large amounts of drug, however, can increase the likelihood and severity of side effects and can be otherwise disadvantageous, e.g., increased costs of therapy. One approach to addressing this issue is to use site-specific drug delivery, which can involve the use of a catheter positioned at a treatment site. Delivery of drug to a site within a tissue/organ, however, generally requires breaking the surface of the organ to implant the catheter tip within the tissue/organ. This may be undesirable where the tissue/organ is sensitive or already damaged and may compromise the integrity of structures surrounding the tissue/organ. Thus, other methods for tissue- or organ-specific drug delivery would be desirable.

The kidney is an organ of particular interest for organ-specific therapy. Diabetic nephropathy, for example, is a disease that develops over a prolonged period, 10-15 years, during which the ability of the kidneys to properly function diminishes. Diabetic nephropathy eventually leads to end-stage renal disease (ESRD), a condition that requires the individual to undergo dialysis or a kidney transplant to stay alive. A therapy that can slow or prevent patients from developing ESRD, or any other tissue or organ specific disease or disorder, without delivering high amounts of drug systemically would be extremely useful. The present invention provides such a therapy.

SUMMARY

Thus, in one aspect the present invention relates to a A drug delivery system, comprising:

a plurality of narrow polydispersity microparticles, wherein the microparticles comprise a polymer selected from the group consisting of poly(lactide-co-glycolide-co-caprolactone), poly(lactide-bl-glycolide), poly(lactide-co-glycolide)-bl-polyethyleneglycol, poly(lactide-co-glycolide)-bl-polyethylene glycol-bl-poly(lactide-co-glycolide), poly(lactide-co-glycolide-co-caprolactone), poly(lactide-co-glycolide-co-hydroxybutyric acid), poly(lactide-co-glycolide-co-trimethylene carbonate), poly(lactide-co-glycolide)-bl-polycaprolactone, poly(lactide-co-glycolide)-bl-poly(hydroxybutyric acid), poly(lactide-co-glycolide)-bl-poly(methylene carbonate) and blends of two or more of the preceding; and, a bioactive agent adhered to surfaces of, incorporated into or integrated into the structure of the microparticles.

In an aspect of the present invention, the lactide is selected from the group consisting of l-lactide, d-lactide, d,l-lactide or meso-lactide.

In an aspect of the present invention, the microparticles have a mean particle size of about 8 to about 20 microns.

In an aspect of the present invention, the microparticles have a mean particle size of about 10 to about 15 microns.

In an aspect of the present invention, the microparticles are substantially spherical and the mean particle size is a mean diameter.

In an aspect of the present invention, the mole percent of caprolactone in the poly(lactide-co-glycolide-co-caprolactone) is about 10% to about 70%.

In an aspect of the present invention, the mole percent of caprolactone in the poly(lactide-co-glycolide-co-caprolactone) is less than about 50%.

In an aspect of the present invention, the mole percent of glycolide in the poly(lactide-co-glycolide-co-caprolactone) is about 10% to about 50%.

In an aspect of the present invention, the mole percent of glycolide in the poly(lactide-co-glycolide-co-caprolactone) is less than 50%.

In an aspect of the present invention, the mole percent of lactide in the poly(lactide-co-glycolide-co-caprolactone) is more than about 50%.

In an aspect of the present invention, the mole percent of glycolide in the poly(lactide-co-glycolide)-bl-polyethylene glycol is about 10-50%.

In an aspect of the present invention, the mole percent of glycolide in the poly(lactide-co-glycolide)-bl-polyethylene glycol is less than 50%.

In an aspect of the present invention, the mole percent of polyethylene glycol in the poly(lactide-co-glycolide)-bl-polyethylene glycol is about 1-50%.

In an aspect of the present invention, the mole percent of lactide in the poly(lactide-glycolide)-bl-polyethylene glycol is about 50% to about 90%.

In an aspect of the present invention, the bioactive agent is selected from the group consisting of a TGF-β pathway inhibitor, a protein kinase C pathway inhibitor, a CTGF pathway inhibitor, an mTOR pathway inhibitor, an antibody against TGF-β, an antibody against CTGF, an angiotensin-converting enzyme inhibitor, an angiotensin II receptor blocker, a diuretic, a beta-blocker, a calcium channel blocker, a vasodilator, a direct renin inhibitor, erythropoietin, an inhibitor of AGE-RAGE signaling, an inhibitor of SMAD signaling, iron and immunosuppresives.

In an aspect of the present invention, the TGF-β pathway inhibitor is halofuginone.

In an aspect of the present invention, the protein kinase C pathway inhibitor is reboxistaurin.

In an aspect of the present invention, the mTOR inhibitor is selected from the group consisting of sirolimus, everolimus, zotarolimus, pimecrolimus, temsirolimus and biolimus.

An aspect of the present invention is a method of treating a disease comprising administering the drug delivery system of claim 1 into the artery of a patient in need thereof, wherein less than 10% of the microparticles degrade under physiological conditions to release a therapeutic amount of the bioactive agent within 1 week of administration and more than 90% of the microparticles degrade under physiological conditions to release a therapeutic amount of the bioactive agent within 12 months of administration.

In an aspect of this invention, in the above method, the microparticles have a mean diameter such that at least 80% of them are trapped in glomeruli of the kidney on a first pass.

In an aspect of this invention, in the above method, at least 90% of the microparticles are trapped in the glomeruli of the kidney on the first pass.

In an aspect of this invention, in the above method, at least 99% of the microparticles are trapped in the glomeruli of the kidney on the first pass.

In an aspect of this invention, in the above method, the disease is a kidney disease selected from a group consisting of chronic kidney disease, diabetic nephropathy, focal segmental glomerulosclerosis, IgA Nephritis, lupus nephritis, reflux nephropathy, glomerulonephritis, glomerulonephrosis and polycystic renal disease.

An aspect of this invention is a method comprising dissolving a polymer and a hydrophobic bioactive agent in a water immiscible solvent mixture comprising at least one solvent with a boiling point less than about 60° C. and at least one solvent with a boiling point more than about 60° C. to make an organic phase solution; adding the organic phase solution under high shear to an aqueous phase and sonicating to form an emulsion; passing the emulsion through a porous membrane of a selected pore size; removing the organic solvents; and creating a release rate curve for the bioactive agent from the resulting microparticles.

In an aspect of this invention, in the above method, if a slower release rate is desired, the relative amount of the solvent with a boiling point more than about 60° C. is decreased within the solvent mixture.

In an aspect of this invention, in the above method, if a faster release rate is desired, the relative amount of the solvent with a boiling point more than about 60° C. is increased within the solvent mixture.

In an aspect of this invention, in the above method, the solvent with a boiling point less than about 60° C. comprises dichloromethane or chloroform.

In an aspect of this invention, in the above method, the solvent with a boiling point more than about 60° C. comprises ethyl acetate, methyl ethyl ketone or methyl isobutyl ketone.

In an aspect of this invention, in the above method, the solvent mixture comprises 90/10 dichloromethane/ethyl acetate.

In an aspect of this invention, in the above method, the solvent mixture comprises 80/20 dichloromethane/ethyl acetate.

In an aspect of this invention, in the above method, the bioactive agent is selected from the group consisting of a TGF-β pathway inhibitor, a protein kinase C pathway inhibitor, a CTGF pathway inhibitor, an mTOR pathway inhibitor, an antibody against TGF-β, an antibody against CTGF, an angiotensin-converting enzyme inhibitor, an angiotensin II receptor blocker, a diuretic, a beta-blocker, a calcium channel blocker, a vasodilator, a direct renin inhibitor, erythropoietin, an inhibitor of AGE-RAGE signaling, an inhibitor of SMAD signaling, iron and immunosuppresives.

In an aspect of this invention, in the above method, the TGF-β pathway inhibitor is halofuginone.

In an aspect of this invention, in the above method, the protein kinase C pathway inhibitor is reboxistaurin.

In an aspect of this invention, in the above method, the mTOR inhibitor is selected from the group consisting of sirolimus, everolimus, zotarolimus, pimecrolimus, temsirolimus and biolimus.

DETAILED DESCRIPTION

Brief Description of the Figures

FIG. 1 is a graphical representation of drug release rate as a function of the solvent used to create the drug/matrix medium.

DISCUSSION

It is understood that use of the singular herein includes the plural and vice versa unless expressly stated otherwise. That is, "a" and "the" are to be construed as referring to one or more of whatever the word modifies. For example, "a" therapeutic agent is understood to include one such agent, two such agents or, under the right circumstances as determined by those skilled in the treatment of diseased tissues, even more such agents, again, unless it is expressly stated or is unambiguously obvious from the context that such is not intended.

As used herein, "substantial" or "substantially" means that the object of the adjective or adverb may not be a perfect example of such object but would still be immediately envisaged by the skilled artisan to warrant the general designation. That is, when modified by the word "substantially," it is understood that the object of the modifier would be considered close enough to be recognized by those of ordinary skill in the art as being within the general genus of such objects. For example, "substantially spherical" refers to an object that, while not a mathematically perfect sphere, would be easily recognized as being within reasonable bounds of that which those skilled in the art would readily consider "spherical."

The use of other words of approximation herein, such as "about" or "approximately" when used to describe numerical values or ranges likewise are understood to mean that those skilled in the art would readily consider a value different from the exact number or outside the actual range to be close enough to be within the aegis of that number or range. At the very least, "about" or approximately is understood to mean±15% of a given numerical value or range starting and ending point.

As used herein, "polydispersity" refers to the range of sizes of microparticles within a particular microparticle population. That is, an extremely polydisperse population might involve particles having a mean size of, say, 10 microns with individual particles ranging from 1 to 100 microns. For the purposes of this invention, a "narrow polydispersity" is preferred. That is, given a particular mean particle size, it is presently preferred that individual particles in the population differ by no more than ±20%, preferably no more than ±15% and most preferably at present no more than ±10% from the mean particle size. More specifically, a microparticle population of this invention preferably has a mean particle size of about 8 to about 20 microns, more preferably at present from about 10 to about 15 microns. Thus, if a mean particle size of 12.5 microns is selected, individual particles in the population would most preferably be within the range of from about 11 to about 13 microns.

As used herein, "microparticle" refers to a polymeric solid that can have any desired shape such as, without limitation, spherical, ellipsoid, rod-like, entirely random shaped, etc., although substantially spherical microparticles are well-known in the art, are readily prepared and are presently preferred. The polymers of which the microparticles are made are biocompatible and may be biostable or biodegradable.

As used herein, "biocompatible" refers to a material that in its original intact state and when biologically decomposed into its degradation products is not toxic or at least is minimally toxic to living tissue. A biocompatible material does not, or at least minimally and reparably, injure living tissue. Further, a biocompatible material does not, or at least minimally and controllably, cause an immunological reaction in living tissue.

By 'biostable" is meant that the material of which a microparticle herein is comprised does not appreciably decompose over relatively long periods of time which may reach many years in a physiological environment, for example, without limitation, at physiological pHs or in the presence of enzymes.

As used herein, "biodegradable" refers to a polymer that decomposes under physiological conditions such as body temperature, pH, enzyme activity and the like and thereafter is absorbed or eliminated by a patient's body, the foregoing occurring over a relatively short period of time that may be as short as hours or up to a year or more.

Microparticles herein may be solid or they may be porous so as to provide a large surface area to which bioactive agents may be physically or chemically adhered or to facilitate elution of the bioactive agent from within the particles by rendering the interior of the particles closer to a surface in contact with the external environment.

As used herein, "mean particle size" is arrived at by measuring the size of each individual microparticle and then dividing by the total number of microparticles. To accomplish this generally requires sophisticated equipment and techniques but such are well-known and readily available to those skilled in the art; that is, determination of mean particle size is commonplace in the art. To assure efficient capture of the microparticles of this invention at the capillary bed of a tissue/organ, e.g., glumeruli in the kidneys, not only should the microparticles have the stated mean particle size but the polydispersity of the microparticles should be as narrow as can be achieved, that is, as close to monodisperse as possible. While several techniques are discussed below for arriving at relatively narrow size distributions, as technology advances equipment and procedures for attaining even narrower size distributions will likely become available and all such equipment, procedures and size distributions are within the scope of this invention.

When the microparticles herein are substantially spherical, a presently preferred configuration, mean particle size is synonymous with mean diameter.

The microparticles of this invention are sized to be entrapped by the capillary system of an organ, although it is possible to adjust particle size upward, i.e., to use larger particles, if such would be more advantageous for the treatment of a particular tissue or organ disease to entrap the particles in a larger vessel.

The reason for selecting the capillaries as a presently preferred target for the entrapment of microparticles of this invention lies in the physiology of the capillary system. That is, the capillary system comprises a vast network of minute (averaging approximately 1 millimeter in length and 8 microns in diameter) vessels that permeates virtually every tissue in the mammalian body. As testament to the ubiquity of capillaries, it has been estimated that their number in the average human body is approximately 19,000,000,000 and that most living tissue cells lie within 1-3 cell lengths of a capillary. Thus, to achieve maximum deployment of a bioactive agent in a target tissue, it makes sense that the vehicle carrying the bioactive agent be capable of maneuvering through the circulatory system to the capillary level. Entrapping the microparticles at the capillary level assures that the target disease tissue receives the maximum benefit of the bioactive agent attached to or adhered to the surface of the microparticles.

To assure that microparticles herein are delivered to the desired capillary system, the microparticles containing an appropriate bioactive agent or combination of agents are administered into an artery that directly services a tissue/organ of interest. By "directly services" it is meant that blood flowing through the artery proceeds in a single direction through the labyrinthine maze comprising artery→arterioles→metarterioles→capillaries→postcapillary venules→venules—vein such that, once placed into the artery, microparticles have nowhere to go but to the capillaries of the target tissue/organ. It is noted that the kidneys have a rather unique circulatory system: arteries→afferent arterioles→glomerular capillaries→efferent arterioles and the methods of this invention are eminently suitable for use in treating the kidneys. It is noted that arterioles are generally regarded as having interior diameters in the range of approximately 10 to 50 microns, metarterioles about 10 to 20 microns and capillaries approximately 4 to 15 (average about 8) microns in diameter. Thus, microparticles having a mean size of about 10 to 15 micrometers should be efficiently entrapped once they reach the capillaries.

As noted previously, however, while capillaries are a presently preferred entrapment region, if desired the methods and particle sizes of this invention can be readily modified by those skilled in the art to effect entrapment in the lumen of any size vessel found at a target location.

It is presently preferred that at least 80% of microparticles, more preferably at least 90% and most preferably at least 99% of microparticles administered into an artery of a patient will be entrapped at a target location, preferably that of the capillary bed. It is understood that any tissues of interest can be treated with microparticles of the invention, although the treatment of the kidney is presently preferred.

As used herein, "incorporated into" a microparticle refers to a bioactive agent that is physically entrapped within the matrix formed by the polymer forming the particle.

As used herein, "adhered to a surface" of a microparticle refers a bioactive agent that is chemically or physically attached to a surface of a particle that is in direct contact with the external environment.

As used herein, "integrated into the structure" of a microparticle refers to a bioactive agent that is a part of the chemical structure of the polymer forming the microparticle.

As used herein, "bioactive agent" refers to any substance that, when administered in a therapeutically effective amount to a patient suffering from a disease, has a therapeutic beneficial effect on the health and well-being of the patient. A therapeutic beneficial effect on the health and well-being of a patient includes, but is not limited to: (1) curing the disease; (2) slowing the progress of the disease; (3) causing the disease to regress; or (4) alleviating one or more symptoms of the disease. The terms "bioactive agent", "therapeutic agent" and "drug" can be used interchangeably herein unless the context dictates otherwise.

As used herein, a bioactive agent also includes any substance that has a prophylactic beneficial effect on the health and well-being of the patient, when administered to a patient known or suspected of being particularly susceptible to a disease. A prophylactic beneficial effect includes, but is not limited to: (1) preventing or delaying on-set of a disease; (2) maintaining a disease at a regressed level once such level has been achieved by a therapeutically effective amount of a therapeutic agent, which may be the same as or different from the therapeutic agent used in a prophylactically effective amount; or (3) preventing or delaying recurrence of a disease after a course of treatment with a therapeutically effective amount of a therapeutic agent, which may be the same as or different from the therapeutic agent used in a prophylactically effective amount.

The amount of bioactive agent in microparticles of the invention will depend on the required minimum effective concentration (MEC) of the agent and the length of time over which it is desired that the MEC be maintained. As used herein, "MEC" refers to the minimal blood or tissue level at which an agent exerts the desired effect. For most bioactive agents the MEC will be known, or readily derivable by those skilled in the art from the literature. For experimental bioactive agents or those for which the MEC by localized delivery is not known, such can be empirically determined using techniques well-known to those skilled in the art.

Bioactive agents can be incorporated into microparticles of this invention by a number of techniques well-known in the art. For example, without limitation, a bioactive agent may be dissolved (if it is hydrophobic) or suspended (if it is hydrophilic) in an inner organic phase during microparticle fabrication. A bioactive agent (hydrophilic) can form an emulsion with an organic phase then form a secondary emulsion in a water phase. Or a bioactive agent can be incorporated into microparticles through a series of secondary steps where the finished microparticles are flooded with an agent-containing solution and then dried, typically by lyophilization. Another alternative would be to affix a bioactive agent by, chemical means to the surface of a microparticle. Also, particles can be prepared by spraying a solution of a polymer/drug in a low volatility solvent into a heated chamber so the solvent is rapidly evaporated, leaving the polymer/drug as a small particle. The size of the particle can be adjusted by changing the polymer concentration, the spray rate and/or the type and setting of the spray nozzle. This process can be further refined by using a laminar flow jet technology combined with an electrostatic field, a vibrating nozzle and or a coaxial fluid (gas or liquid non-solvent). Other suitable methods will be easily discernable to those skilled in the art using the disclosures herein and are encompassed by the present invention.

Any manner of bioactive agent that is known or suspected to have a beneficial effect on a diseased tissue or organ may be used with the method of this invention. Thus, a bioactive agent may be selected from, without limitation, an anti-restenotic, an antiproliferative, an anti-inflammatory, an antineoplastic, an antimitotic, an antiplatelet, an anticoagulant, an antifibrin, an antithrombin, a cytostatic, an antibiotic, an anti-allergenic, an anti-enzymatic, an angiogenic, a cyto-protective, a cardioprotective, a proliferative, an ABC A1 agonistic or an antioxidative agent or any combination thereof. Presently preferred bioactive agents include, without limitation, antibiotics, antifungals, anti-virals and anti-fibrotics.

Examples of antibiotics include, without limitation, ampicillin, ampicillin/sulbactam, amoxicillin, amoxicillin/clavulanate, azithromycin, aztreonam, cefaclor, cefadroxil, cefazolin, cefdinir, cefepime, cefixime, cefoperazone, cefotaxime, cefotetan, cefoxitin, cefpodoxime, cefprozil, ceftazidime, ceftibuten, ceftizoxime, ceftriaxone, cefuroxime, cefuroxime, cephalexin, chloramphenicol, ciprofloxacin, ciprofloxacin, clarithromycin, clindamycin, cloxacillin, dapsone, dicloxacillin, doxycycline, erythromycin, ethambutol, fosfomycin gatifloxacin, imipenem/cilastatin, isoniazid, levofloxacin, linezolid, loracarbef, meropenem, metronidazole, minocycline, moxifloxacin, nitrofurantoin, nafcillin, norfloxacin, penicillin, piperacillin, piperacillin/tazobactam, pyrazinamide, quinupristin/dalfopristin, rifampin, tetracycline, ticarcillin, ticarcillin/clavulanate, tmp/smx and trimethoprim.

Examples of antivirals include, without limitation, amprenavir, delavirdine, didanosine, efavirenz, famciclovir, ganciclovir, indinavir, lamivudine, lamivudine/zidovudine, nelfinavir, nevirapine, ritonavir, saquinavir, stavudine, valacyclovir, zalcitabine, zidovudine.

Examples of anti-fungals include, without limitation, caspofungin, fluconazole, flucytosine, itraconazole, terbinafine, voriconazole.

Examples of anti-fibrotics include, without limitation, inhibitors of the TGF-β pathway, for example halofuginone and monoclonal antibodies against TGF-β or its receptor, protein kinase C inhibitors such as ruboxistaurin, CTGF inhibitors such as FG-3019 and metalloproteinase-ADAM-10 inhibitors such as XL-784.

Other compounds that may be used as bioactive agents of this invention include, without limitation, allopurinol, carbamazepine, cetirizine, cimetidine, famotidine, fexofenadine, gabapentin, ketorolac, metoclopramide, primidone, ranitidine, sotalol, tirofiban and paracalcitol (Zemplar®).

It is presently particularly preferred that the bioactive agent be selected from the group of a TGF-β pathway inhibitor, a protein kinase C pathway inhibitor, a CTGF pathway inhibitor, an mTOR pathway inhibitor, an antibody against TGF-β, an antibody against CTGF, an angiotensin-converting enzyme inhibitor, an angiotensin II receptor blocker, a diuretic, a beta-blocker, a calcium channel blocker, a vasodilator, a direct renin inhibitor, erythropoietin, an inhibitor of AGE-RAGE signaling, an inhibitor of SMAD signaling, iron and immunosuppresives.

The presently preferable TGF-β pathway inhibitor is halofuginone, the protein kinase C pathway inhibitor is reboxistaurin and the mTOR inhibitor is selected from a group that includes sirolimus, everolimus, zotarolimus, pimecrolimus, temsirolimus and biolimus.

As used herein, "treating" refers to the administration of a therapeutically effective amount of a bioactive agent to a patient known or suspected to be suffering from a tissue/organ disease.

As used herein, "patient" refers to any organism that can benefit from the administration of a bioactive agent. For example, without limitation, a patient refers to a mammal such as, without limitation, a cat, dog, horse, cow, pig, sheep, rabbit, goat, or, preferably at present, a human being.

As used herein, a "therapeutically effective amount" refers to the amount of bioactive agent that has a beneficial effect, which may be curative or palliative, on the health and well-being of a patient with regard to a tissue/organ disease with which the patient is known or suspected to be afflicted. A therapeutically effective amount may be administered as a single bolus, as intermittent bolus charges, as short, medium or long term sustained release formulations or as any combination of these.

As used herein, "mole percent" refers to the percent of a polymer unit present within a block co-polymer of the invention, wherein the amount of each polymer unit is measured in moles. For example, if there is a block-copolymer of the form (A-B)—(C) where the polymer unit A is present in 10 moles, B is present in 20 moles and C is present in 70 moles, then the mole percent of A would be 10 moles/(10 moles+20 moles+70 moles) which equals a mole percent of 10%.

The microparticles of this invention comprise either terpolymers or A-B or A-B-A block copolymers. While other monomers that provide the same benefits as the following may be used and are within the scope of this invention, it is presently preferred that the terpolymer is poly(lactide-coglycolide-co-caprolactone). The terpolymer may be an alternating, random alternating or purely random copolymer or a block copolymer. It is also presently preferred that the A block of the block copolymers comprise lactide or a lactide/glycolide copolymer (PLGA), which may be an alternating, purely random or a lactide-bl-glycolide block to ultimately create a block-within-a-block configuration where the B-block comprises glycolide (if the A block comprises lactide but not glycolide), poly(ethylene glycol) (PEG) or caprolactone (PCL).

As used herein, an alternating polymer has the general structure: . . . x-y-z-x-y-z-x-y-z- . . . while a random alternating polymer has the general structure: . . . x-y-x-z-x-y-z-y-z-x-y- . . . and a purely random polymer has the general structure x-y-z-y-z-y-z-x-x-z-y . . . , it being understood that the exact juxtaposition of the various constitutional x, y and z units may vary. A regular block polymer has the general structure: . . . x-x-x-y-y-y-z-z-z-x-x-x . . . , while a random block polymer has the general structure: . . . x-x-x-z-z-x-x-y-y-y-y-z-z-z-x-x-z-z-z- . . . . Similar to the situation above regarding regular and alternating polymers, the juxtaposition of blocks, the number of constitutional units in each block and the number of blocks in block polymers of this invention are not in any manner limited by the preceding illustrative generic structures.

It is presently preferred that the block copolymer used to construct microparticles of this invention be selected from the group: poly(lactide-bl-glycolide), poly(lactide-co-glycolide)-bl-polyethyleneglycol, poly(lactide-co-glycolide)-bl-poly(ethyleneglycol)-bl-poly(lactide-co-glycolide), poly(lactide-co-glycolide-co-caprolactone), poly(lactide-co-glycolide-co-hydroxybutyric acid), poly(lactide-co-glycolide-co-trimethylenecarbonate), poly(lactide-co-glycolide)-bl-polycaprolactone, poly(lactide-co-glycolide)-bl-poly(hydroxybutyric acid), poly(lactide-co-glycolide)-bl-poly(methylene carbonate) and blends of two or more of the preceding. The lactide may be d,l-lactide, l-lactide, d-lactide or meso-lactide.

Glycolide can provide an accelerated or enhanced degradation of the block co-polymer while lactide can provide mechanical strength. Thus, by varying the ratio of glycolide and lactide, the degradation rate of the copolymer can be optimized. The polyethylene glycol) unit, on the other hand, can provide water solubility, thus adding another measure of controlling the degradation rate of the copolymer and in turn the agent release rate.

In presently preferred embodiments, the mole percent of glycolide in the poly(lactide-co-glycolide)-bl-polyethylene glycol will be less than about 50%, preferably at present between about 10% and about 30%. The mole percent of polyethylene glycol in the poly(lactide-co-glycolide)-bl-polyethylene glycol is about 1-50%, preferably at present between about 1% and about 10%. Further, the mole percent of lactide in the poly(lactide-glycolide)-bl-polyethylene glycol) is more than 50%, preferably at present between about 70 and 90 mole percent. The exact molar amounts of each component will depend on the desired mechanical strength, degradation rate and hydrophilicity of the microparticles to be used for a particular application. Determining each of these parameters is well within the capabilities of those of ordinary skill in the art based on the disclosures herein and would not require undue experimentation.

As noted above, the present invention also provides for PLGA-PCL terpolymer-based microparticles. The presence of caprolactone in the terpolymer can increase the miscibility of the bioactive agent with the polymer matrix and therefore better control release of the agent. Caprolactone-derived constitutional units in the terpolymer can also provide a hydrophobic entity for better phase mixing with hydrophobic drugs and increase diffusivity of the terpolymer by lowering the glass transition temperature of the polymers. For example, the higher the capolactone content, the lower the Tg of the resultant terpolymer. As also noted previously, glycolide can bestow an accelerated or enhanced degradation rate on the terpolymer while lactide provides mechanical strength.

It is presently preferred that the mole percent of caprolactone in the terpolymer be about 10% to about 70%, preferably at present less than about 50% unless burst release of the bioactive agent is desired. Glycolide content can range from about 10% to about 50%, although about 10% to about 40% is presently preferred. The mole percent of lactide in the terpolymer is at least 50%, preferably at present between about 70 and about 90 mole percent.

While the mole percent of various polymer units can be varied and preferred amounts are set forth herein, the final block copolymer will also have a preferred molecular weight. Specifically, the preferred molecular weight of the poly(lactide-co-glycolide-co-caprolactone) terpolymer will be between about 10-200 kDa and more preferably between about 70 and 150 kDa. The preferred molecular weight of the poly(lactide-co-glycolide)-bl-polyethylene glycol polymer will be between about 10-200 kDa and more preferably between about 70 and 150 kDa.

The present invention also provides a method for treating a disease that involves administering bioactive agent-loaded microparticles into an organ-specific artery, that is, an artery that services a particular tissue/organ of a patient in need thereof. The population of microparticles will have a mean diameter such that they will become lodged in the capillaries of target tissues and most preferably in the glomeruli of nephrons of the kidneys, as described above.

The plurality of microparticles can comprise bioactive agents in several different ways. In the simplest, the bioactive agent is adhered to, incorporated into or integrated into the structure of microparticles at a single concentration so that all microparticles in a population are substantially the same with regard to bioactive agent load. In another approach, the bioactive agent is adhered to the surface of, incorporated into or integrated into the structure of the microparticles or, if desired into different microparticles, at different concentrations in separate preparations and the microparticles formed in those separate preparations can be combined into a single population for administration to a patient. In yet another approach, different bioactive agents can be separately adhered to the surface of, incorporated into or integrated into the structure of the microparticles, or again, if desired in different microparticles, at various concentrations, the microparticles again being combined for administration. Two or more bioactive agents can, of course, be adhered to the surface of, incorporated into or integrated into the structure of the same microparticle such that the resulting microparticles each contain more than one bioactive agent. Those skilled in the art will, based on the disclosure herein, be able to devise additional combinations of microparticles and bioactive agent(s): and all such combinations are within the scope of this invention.

As mentioned above, in order to achieve the preceding degrees of entrapment it is necessary to produce microparticles having a size distribution as narrow as possible around a selected mean size wherein the mean size is determined by the vessel lumen size present in the tissue being treated. For instance, the average particle size must be small enough to pass through an afferent arteriole (in the case where a kidney is the target tissue) but large enough to be trapped by a capillary. While there may be other means to accomplish this and any such means is within the scope of this invention, presently preferred means include emulsification followed by supercritical fluid solvent extraction, electrohydrodynamic atomization and membrane emulsification.

Emulsification followed by supercritical fluid solvent extraction to form microparticles having a very narrow size range is a well-known technique in the art and therefore need not be extensively discussed herein. In brief; the technique involves the formation of an emulsion by dissolving a polymer and a therapeutic agent in a solvent for both, adding the solution under high shear to water containing emulsifying agent, sonicating to achieve a narrow droplet size range, passing the droplets through a porous membrane of well-defined pore size and then extracting the solvent from the microparticles using a supercritical fluid to give a hardened particle. A supercritical fluid, that is a fluid above its critical temperature and pressure, is used because of the physical properties of such fluids, which are intermediate between those of a gas and those of a liquid. For example, supercritical carbon dioxide has a viscosity in the range of about 0.02 to about 0.1 centipoise (cP) whereas liquids have viscosities of 0.5-1.0 cP and gasses have viscosities around 0.01 cP. Further, the diffusivities of solutes in supercritical carbon dioxide are up to a factor of 10 higher than in liquid solvents. This and the tunability of the solvating properties of supercritical fluids, which are a complex (but relatively well-understood) function of pressure and temperature, permit extremely selective extraction of one material, the solvent herein for instance, from others it may be combined with.

In any event, the hardened microparticles obtained after supercritical fluid solvent extraction may then be passed through yet another filter, with well-defined pore size to still further control particle size distribution.

Electrohydrodynamic atomization (EDHA) is another relatively new but nevertheless well-characterized technique in the art for producing narrow size distribution, i.e., essentially monodisperse, microparticles. Briefly, electrohydrodynamic atomization involves pumping a solution through a nozzle wherein a high voltage potential has been established between the tip of the nozzle and a counter-electrode. The high potential causes a build-up of electric charge in droplets at the nozzle tip and when the coulombic forces exceed the surface tension of the droplets, they separate, essentially explode, into smaller droplets. If parameters are optimized to achieve a stable spray, monodispersed droplets are obtained. Removal of solvent from the droplets yields monodisperse solid microparticles. Parameters that may be varied to achieve a particular average size droplet/particle include, without limitation, the applied voltage, the flow rate, density and conductivity.

Normal emulsification techniques generally afford droplets of relative polydispersity, at least with regard to the narrow size distribution desired for use in the current invention. Thus, one and perhaps two filtrations as set forth above with regard to emulsification/supercritical fluid solvent extraction are required.

Membrane emulsification is another relatively new technique for producing essentially monodisperse microparticles. As with standard emulsification followed by multiple filtrations and electrohydrodynamic atomization, membrane emulsification, while a relatively recent development, is well-known to those skilled in the art. Briefly, membrane emulsification involves the injection of an intended discontinuous phase through a porous membrane in which pore size is very carefully controlled into the intended continuous phase, which is moving past the porous membrane on the side opposite that from which the discontinuous phase is being injected. Droplets are sheared off the membrane by the moving continuous phase. Control of droplet size is quite exquisite compared to normal emulsification techniques because size is determined predominantly by easily varied parameters including the speed of the continuous phase, viscosity of the continuous phase, interfacial tension between the phases, the chemistry of the system—surfactant type and physical properties of all the constituents—and, of course, pore size. Newer techniques for creating porous membranes with very defined pore size such as laser drilling and lithographic procedures have made membrane emulsification even more attractive as a technique for control of particle size distribution.

No matter which method is used, the drug delivery system of the invention can be used to treat a range of tissue/organ diseases. It is presently preferred, however, that the diseased organ to be treated be a kidney and the drug delivery system is administered via the renal artery.

By way of example, bioactive agent released at glomeruli of the kidney, specifically everolimus, could reach concentrations of 10 to 150 ng/gram of tissue and in so doing inhibit matrix deposition that contributes to glomerulosclerosis. Methods of the invention, however, are useful for the delivery of such concentrations of agent to any diseased tissue/organ of interest.

Another aspect of the invention relates to a method of controlling the release rate of bioactive agent from a microparticle preparation by varying the solvents used in the preparation of the microparticles. Studies have shown that slower evaporation of solvent, such as would be the case with a 90:10 acetone/methyl ethyl ketone (MEK) mixture, from a medical device coating composition provides faster stent drug release profiles than when a solvent is 100% acetone, which is removed faster during drying. When the solvent removal is slower, the hydrophobic olimus drug has more time to phase separate from the relatively hydrophilic polymer and migrate to the surface, thereby resulting in faster drug release. The present invention builds on these observations.

That is, the method of this invention involves dissolving a polymer and a hydrophobic bioactive agent in a water immiscible solvent mixture comprising at, least one solvent with a boiling point less than about 60° C. and at least one solvent with a boiling point greater than about 60° C. to make an organic phase solution, adding the organic phase solution under high shear to an aqueous phase, sonicating to form an emulsion, passing the emulsion through a porous membrane of a selected pore size and then removing the organic solvents. A release rate curve for the specific polymer/bioactive agent microparticle can then be determined by techniques well known to those skilled in the art. If the release rate is too slow or too fast, manipulating the type and amount of solvents in the solvent mixture will provide either faster or slower release rates. It is understood that the terms slow release and fast release are relative terms measured against one another as they arise from the use of various solvent mixtures within the above parameters.

If a faster release rate is desired, the relative amount of the solvent with a boiling point above about 60° C. is increased. Solvent with a boiling point more than about 60° C. include, without limitation, MEK and methyl isobutyl ketone (MIBK) as shown in FIG. 1.

If a faster release rate is desired, the relative amount of the solvent with a boiling point above about 60° C. is decreased, i.e., the amount of the solvent with a boiling point less than about 60° C. would have to be increased. Solvents with a boiling point less than about 60° C. include, without limitation, chloroform and dichloromethane.

A presently preferred solvent mixture is dichloromethane/ ethyl acetate. By varying the ratio of dichloromethane to ethyl acetate, the release of drug from microparticles can be optimized. An example, without limitation, is 90/10 or 80/20 dichloromethane/ethyl acetate.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating a kidney disease comprising:
    administering into an artery directly servicing the kidney glomeruli of a patient in need thereof, microparticles comprising a bioactive agent, wherein the microparticles comprise a polymer selected from the group consisting of poly(lactide-co-glycolide-co-caprolactone), poly(lactide-bl-glycolide), poly(lactide-co-glycolide)-bl-polyethyleneglycol, poly(lactide-co-glycolide)-bl-polyethyleneglycol-bl-poly(lactide-co-glycolide), poly(lactide-co-glycolide-co-caprolactone), poly(lactide-co-glycolide-co-hydroxybutyric acid), poly(lactide-co-glycolide-co-trimethylene carbonate), poly(lactide-co-glycolide)-bl-polycaprolactone, poly(lactide-co-glycolide)-bl-poly(hydroxybutyric acid), poly(lactide-co-glycolide)-bl-poly(methylene carbonate), wherein:
    less than 10% of the microparticles degrade under physiological conditions to release a therapeutic amount of the bioactive agent within 1 week of administration and more than 90% of the microparticles degrade under physiological conditions to release a therapeutic amount of the bioactive agent within 12 months of administration, and
    wherein at least 80% of the microparticles become entrapped in the glomeruli of the kidney upon administration of the microparticles.

2. The method of claim 1, wherein at least 90% of the microparticles become entrapped in the glomeruli of the kidney first upon administration of the microparticles.

3. The method according to claim 1, wherein the kidney disease is selected from the group consisting of chronic kidney disease, diabetic nephropathy, focal segmental glomerulosclerosis, IgA Nephritis, lupus nephritis, reflux nephropathy, glomerulonephritis, glomerulonephrosis and polycystic renal disease.

4. The method according to claim 1, wherein the bioactive agent is selected from the group consisting of a TGF-β pathway inhibitor, a protein kinase C pathway inhibitor, a CTGF pathway inhibitor, an mTOR pathway inhibitor, an antibody against TGF-β, an antibody against CTGF, an angiotensin-converting enzyme inhibitor, an angiotensin II receptor blocker, a diuretic, a beta-blocker, a calcium channel blocker, a vasodilator, a direct renin inhibitor, erythropoietin, an inhibitor of AGE-RAGE signaling, an inhibitor of SMAD signaling, iron and immunosuppresives.

5. The method according to claim 4, wherein the TGF-β pathway inhibitor is halofuginone.

6. The method according to claim 4, wherein the protein kinase C pathway inhibitor is reboxistaurin.

7. The method according to claim 4, wherein the mTOR pathway inhibitor is selected from the group consisting of sirolimus, everolimus, zotarolimus, pimecrolimus, temsirolimus and biolimus.

8. The method according to claim 1, wherein the microparticles have a mean particle size of about 8 to about 20 microns.

9. The method according to claim 1, wherein the microparticles have a mean particle size of about 10 to about 15 microns.

10. The method according to claim 1, wherein the microparticles comprise at least two polymers selected from the group consisting of poly(lactide-co-glycolide-co-caprolactone), poly(lactide-bl-glycolide), poly(lactide-co-glycolide)-bl-polyethyleneglycol, poly(lactide-co-glycolide)-bl-polyethyleneglycol-bl-poly(lactide-co-glycolide), poly(lactide-co-glycolide-co-hydroxybutyric acid), poly(lactide-co-glycolide-co-trimethylene carbonate), poly(lactide-co-glycolide)-bl-polycaprolactone, poly(lactide-co-glycolide)-bl-poly(hydroxybutyric acid), and poly(lactide-co-glycolide)-bl-poly(methylene carbonate).

11. The method according to claim 1, wherein microparticles comprise a polymer selected from the group consisting of poly(lactide-co-glycolide-co-caprolactone) and poly(lactide-co-glycolide)-bl-polycaprolactone.

12. A method of treating a kidney disease comprising:
    administering into an artery directly servicing the kidney glomeruli of a patient in need thereof, microparticles comprising a bioactive agent, wherein the microparticles comprise a polymer selected from the group consisting of poly(lactide-co-glycolide-co-caprolactone), poly(lactide-co-glycolide), poly(lactide-co-glycolide)-bl-polyethyleneglycol, poly(lactide-co-glycolide)-bl-polyethyleneglycol-bl-poly(lactide-co-glycolide), poly(lactide-co-glycolide-co-hydroxybutyric acid), poly(lactide-co-glycolide-co-trimethylene carbonate), poly(lactide-co-glycolide)-bl-polycaprolactone, poly(lactide-co-glycolide)-bl-poly(hydroxybutyric acid), and poly(lactide-co-glycolide)-bl-poly(methylene carbonate), wherein:
    less than 10% of the microparticles degrade under physiological conditions to release a therapeutic amount of the bioactive agent within 1 week of administration and more than 90% of the microparticles degrade under physiological conditions to release a therapeutic amount of the bioactive agent within 12 months of administration,
    wherein the microparticles have a mean particle size of about 8 to 20 microns and a narrow polydispersity such that the individual particles in the population differ by no more than ±20%.

13. The method according to claim 12, wherein the microparticles have a mean particle size of about 10 to about 15 microns.

14. The method according to claim 12, wherein the kidney disease is selected from the group consisting of chronic kidney disease, diabetic nephropathy, focal segmental glomerulosclerosis, IgA Nephritis, lupus nephritis, reflux nephropathy, glomerulonephritis, glomerulonephrosis and polycystic renal disease.

15. The method according to claim 12, wherein the bioactive agent is selected from the group consisting of a TGF-β pathway inhibitor, a protein kinase C pathway inhibitor, a CTGF pathway inhibitor, an mTOR pathway inhibitor, an antibody against TGF-β, an antibody against CTGF, an angiotensin-converting enzyme inhibitor, an angiotensin II receptor blocker, a diuretic, a beta-blocker, a calcium channel blocker, a vasodilator, a direct renin inhibitor, erythropoietin, an inhibitor of AGE-RAGE signaling, an inhibitor of SMAD signaling, iron and immunosuppresives.

16. The method according to claim 12, wherein the mTOR pathway inhibitor is selected from the group consisting of sirolimus, everolimus, zotarolimus, pimecrolimus, temsirolimus and biolimus.

17. The method according to claim 12, wherein the microparticles comprise at least two polymers selected from the group consisting of poly(lactide-co-glycolide-co-caprolactone), poly(lactide-bl-glycolide), poly(lactide-co-glycolide)-bl-polyethyleneglycol, poly(lactide-co-glycolide)-bl-polyethyleneglycol-bl-poly(lactide-co-glycolide), poly(lactide-co-glycolide-co-hydroxybutyric acid), poly(lactide-co-glycolide-co-trimethylene carbonate), poly(lactide-co-glycolide)-bl-polycaprolactone, poly(lactide-co-glycolide)-bl-poly(hydroxybutyric acid), and poly(lactide-co-glycolide)-bl-poly(methylene carbonate).

18. The method according to claim 12, wherein microparticles comprise a polymer selected from the group consisting of poly(lactide-co-glycolide-co-caprolactone) and poly(lactide-co-glycolide)-bl-polycaprolactone.

19. A method of treating a kidney disease comprising: administering into an artery directly servicing the kidney glomeruli of a patient in need thereof, microparticles comprising a bioactive agent, wherein:
 less than 10% of the microparticles degrade under physiological conditions to release a therapeutic amount of the bioactive agent within 1 week of administration and more than 90% of the microparticles degrade under physiological conditions to release a therapeutic amount of the bioactive agent within 12 months of administration, and wherein at least 99% of the microparticles become entrapped in the glomeruli of the kidney upon administration of the microparticles.

20. A method of treating a kidney disease comprising:
administering into an artery directly servicing the kidney glomeruli of a patient in need thereof, microparticles comprising a bioactive agent, wherein the microparticles comprise a polymer selected from the group consisting of poly(lactide-co-glycolide-co-caprolactone), poly(lactide-bl-glycolide), poly(lactide-co-glycolide)-bl-polyethyleneglycol, poly(lactide-co-glycolide)-bl-polyethyleneglycol-bl-poly(lactide-co-glycolide), poly(lactide-co-glycolide-co-hydroxybutyric acid), poly(lactide-co-glycolide-co-trimethylene carbonate), poly(lactide-co-glycolide)-bl-polycaprolactone, poly(lactide-co-glycolide)-bl-poly(hydroxybutyric acid), poly(lactide-co-glycolide)-bl-poly(methylene carbonate), wherein:
 less than 10% of the microparticles degrade under physiological conditions to release a therapeutic amount of the bioactive agent within 1 week of administration and more than 90% of the microparticles degrade under physiological conditions to release a therapeutic amount of the bioactive agent within 12 months of administration, and
 wherein at least 99% of the microparticles become entrapped in the glomeruli of the kidney upon administration upon administration of the microparticles.

* * * * *